(12) United States Patent
Dhillon

(10) Patent No.: US 10,939,922 B2
(45) Date of Patent: Mar. 9, 2021

(54) VARIABLE ANGLE CUTTING GUIDE AND METHOD OF USING THE SAME

(71) Applicant: Wright Medical Technology, Inc., Memphis, TN (US)

(72) Inventor: Braham K. Dhillon, Memphis, TN (US)

(73) Assignee: WRIGHT MEDICAL TECHNOLOGY, INC., Memphis, TN (US)

( * ) Notice: Subject to any disclaimer, the term of this patent is extended or adjusted under 35 U.S.C. 154(b) by 212 days.

(21) Appl. No.: 16/323,954

(22) PCT Filed: Oct. 19, 2016

(86) PCT No.: PCT/US2016/057700
§ 371 (c)(1),
(2) Date: Feb. 7, 2019

(87) PCT Pub. No.: WO2018/075028
PCT Pub. Date: Apr. 26, 2018

(65) Prior Publication Data
US 2019/0167274 A1    Jun. 6, 2019

(51) Int. Cl.
*A61B 17/15* (2006.01)
*A61B 17/17* (2006.01)
*A61B 17/16* (2006.01)

(52) U.S. Cl.
CPC .......... *A61B 17/15* (2013.01); *A61B 17/1775* (2016.11); *A61B 17/1682* (2013.01)

(58) Field of Classification Search
CPC ..... A61B 17/15; A61B 17/151; A61B 17/152; A61B 17/154; A61B 17/155; A61B 17/1682; A61B 17/1775
See application file for complete search history.

(56) References Cited

U.S. PATENT DOCUMENTS

| 5,342,367 A | 8/1994 | Ferrante et al. |
| 5,364,402 A | 11/1994 | Mumme et al. |

(Continued)

FOREIGN PATENT DOCUMENTS

| WO | 2009158522 A1 | 12/2009 |
| WO | 2015105880 A1 | 7/2015 |

OTHER PUBLICATIONS

International Search Report and Written Opinion issued in connection with International Patent Application No. PCT/US2016/057700, dated Jul. 11, 2017, 12 pages.

(Continued)

*Primary Examiner* — Eric S Gibson
(74) *Attorney, Agent, or Firm* — Duane Morris LLP

(57) ABSTRACT

A cutting guide includes a body and a rotatable device. The body includes a top portion, a bottom portion parallel to the top portion, and a side portion connecting the top and the bottom portions. The rotatable device is coupled to one end of the top portion of the body, and includes a pivotal element and a handle. The handle in the rotatable device has a first portion coupled to the pivotal element, and a second portion configured to be rotated around an axis of the pivotal element. Each of the top portion of the body, the side portion of the body, the bottom portion of the body, and the handle has one respective edge providing a respective guide surface for cutting a bone in a surgical procedure.

20 Claims, 14 Drawing Sheets

(56) References Cited

U.S. PATENT DOCUMENTS

| | | | |
|---|---|---|---|
| 5,681,316 A | 10/1997 | DeOrio et al. | |
| 7,931,655 B2 | 4/2011 | Axelson, Jr. et al. | |
| 8,317,797 B2 | 11/2012 | Rasmussen | |
| 8,372,080 B2 | 2/2013 | May et al. | |
| 8,814,875 B2 | 8/2014 | Couture et al. | |
| 9,095,352 B2 | 8/2015 | Fisher et al. | |
| 10,292,713 B2* | 5/2019 | Fallin | A61B 17/151 |
| 10,327,785 B2* | 6/2019 | Bake | A61B 17/15 |
| 10,470,779 B2* | 11/2019 | Fallin | A61B 17/151 |
| 2004/0249385 A1* | 12/2004 | Faoro | A61B 17/157 606/88 |
| 2005/0154394 A1* | 7/2005 | Michalowicz | A61B 17/157 606/87 |
| 2006/0155293 A1 | 7/2006 | McGinley et al. | |
| 2007/0265634 A1* | 11/2007 | Weinstein | A61B 17/15 606/87 |
| 2008/0015604 A1* | 1/2008 | Collazo | A61B 17/8095 606/87 |
| 2013/0096680 A1 | 4/2013 | Ribeiro et al. | |
| 2013/0190766 A1 | 7/2013 | Harris et al. | |
| 2015/0127009 A1* | 5/2015 | Berend | A61B 17/155 606/88 |
| 2015/0305753 A1 | 10/2015 | McGinley et al. | |
| 2016/0199076 A1* | 7/2016 | Fallin | A61B 17/1739 606/281 |
| 2016/0213384 A1* | 7/2016 | Fallin | A61B 17/151 |
| 2016/0361071 A1* | 12/2016 | Mahfouz | A61B 17/15 |
| 2017/0325826 A1* | 11/2017 | Bake | A61B 17/1775 |
| 2019/0099189 A1* | 4/2019 | Fallin | A61B 17/151 |
| 2019/0167274 A1* | 6/2019 | Dhillon | A61B 17/1775 |
| 2020/0078025 A1* | 3/2020 | Fallin | A61B 17/151 |

OTHER PUBLICATIONS

Extended European Search Report issued in connection with European Patent Application No. 16919431.3, dated Feb. 17, 2020, 7 pages.

First Examination Report issued in connection with Australian Patent Application No. 2019229415, dated Apr. 28, 2020, 4 pages.

\* cited by examiner

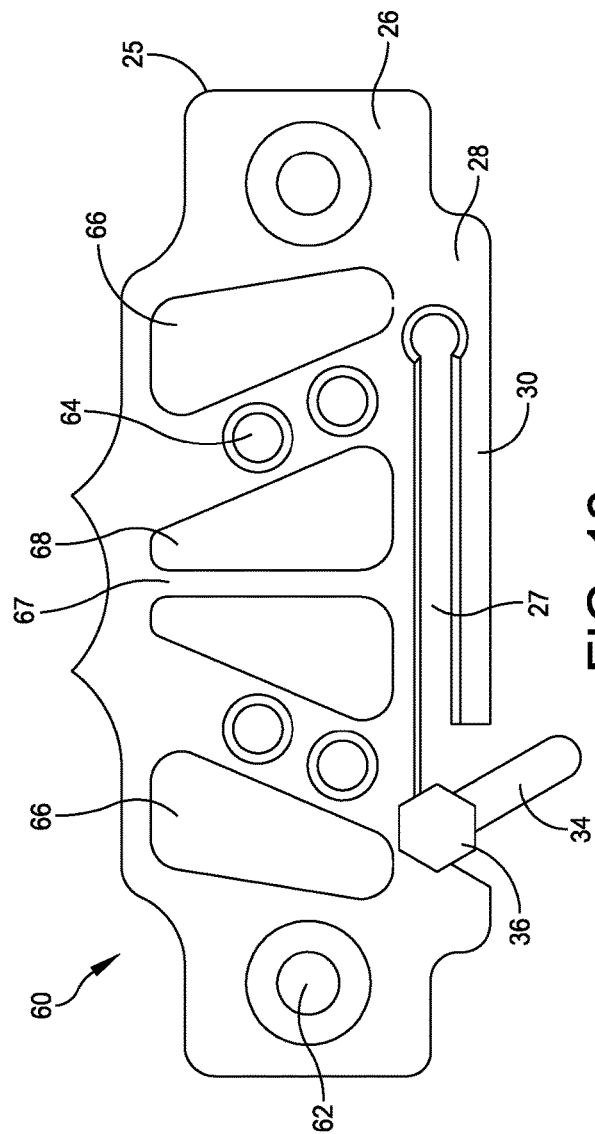
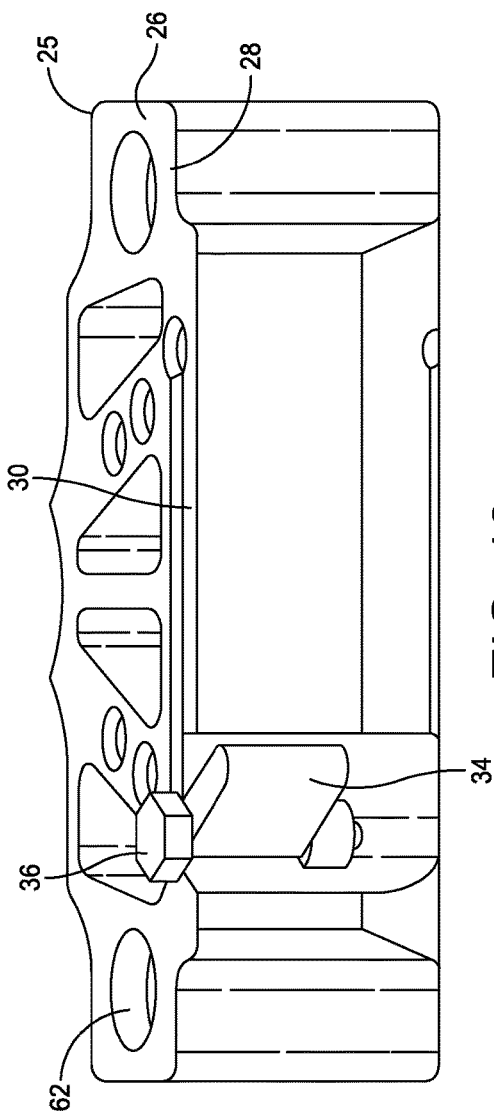
FIG. 12
FIG. 13

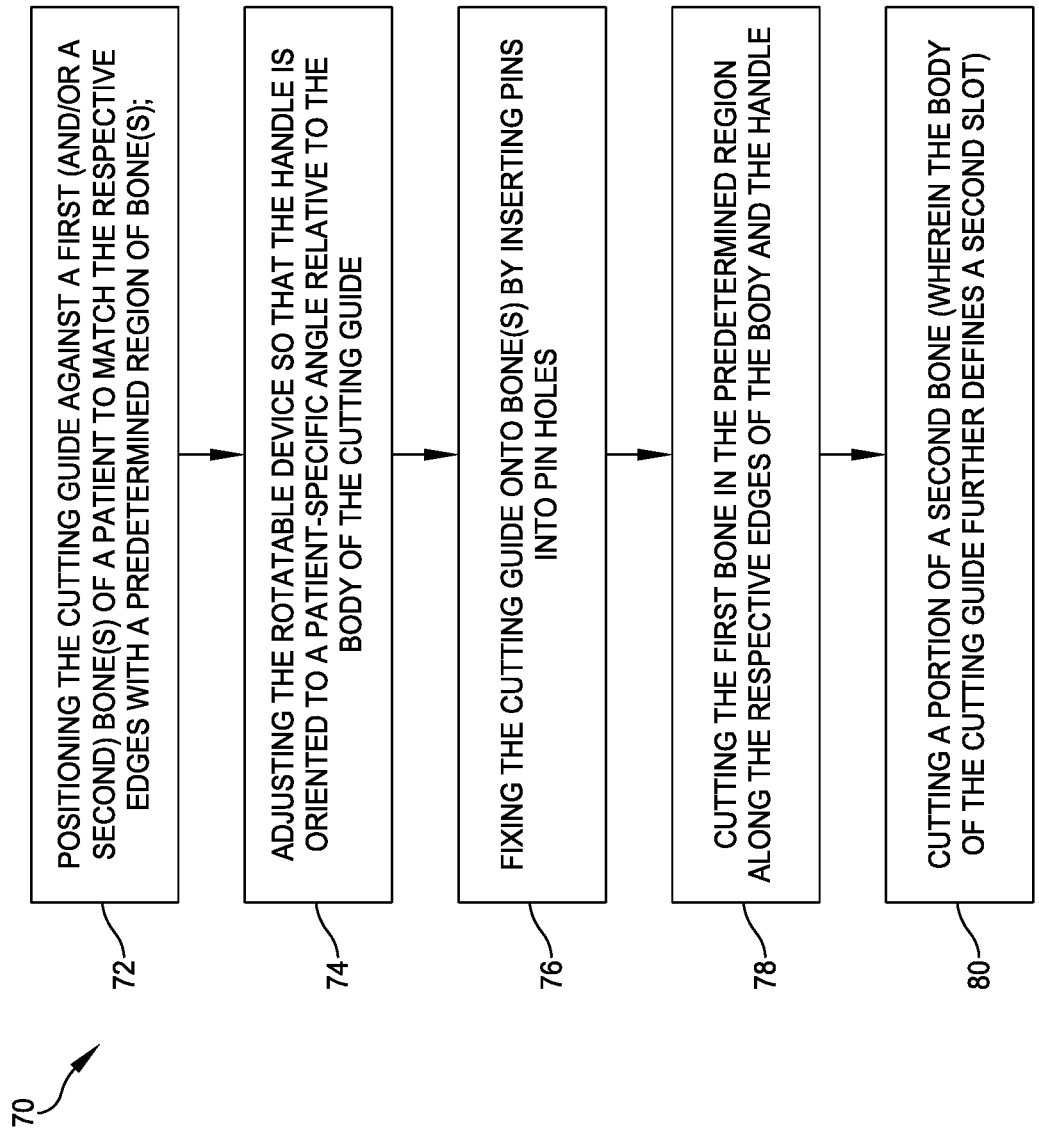

VARIABLE ANGLE CUTTING GUIDE AND METHOD OF USING THE SAME

CROSS-REFERENCE TO RELATED APPLICATION

This application is a U.S. national stage application under 35 U.S.C. § 371 of International Application No. PCT/US2016/057700, filed Oct. 19, 2016, the entirety of which is incorporated herein by reference.

FIELD OF DISCLOSURE

The disclosure relates generally to tools and methods for orthopedic medical implant. More particularly, the disclosed subject matter relates to a cutting guide and a method of using such a cutting guide for cutting a bone in a surgery, for example, for cutting bones of a human foot in a total ankle replacement.

BACKGROUND

Orthopedic implant devices have been utilized to fully or partially replace existing skeletal joints in humans. During surgical procedures, bones need to be cut to implant orthopedic devices.

An ankle is a joint that acts much like a hinge. The ankle joint is formed by the union of three bones: a talus, a tibia and a fibula. The ankle bone is the talus. The top of the talus fits inside a socket that is formed by a lower end of the tibia, and the fibula, the small bone of the lower leg. Arthritis, bone degeneration, and/or injury can cause ankle joint deterioration resulting in pain, reduced range of motion, and decreased quality of life. Options for treating the injured ankle have included anti-inflammatory and pain medications, braces, physical therapy, joint arthrodesis, and total ankle replacement (or arthroplasty).

Total ankle replacement generally comprises two components—a tibial implant and a talar implant. The implants comprise articulation surfaces sized and configured to mimic the range of motion of the ankle joint. For example, the talar implant may comprise an implant sized and configured to mimic the talar dome and the tibial implant may comprise an articulation surface sized and configured to mimic articulation of the tibia. An articulating component may be located between the talar implant and the tibial implant.

SUMMARY OF INVENTION

The present disclosure provides a cutting guide for cutting a bone during a surgical procedure. More particularly, the present disclosure provides a cutting guide configured to provide an adjustable angle, and a method for using the cutting guide, for example, for cutting a bone such as tibia in a surgery of total ankle arthroplasty. The present disclosure also provides a method of making the cutting guide. These include, but are not limited to, the following aspects and embodiments.

In one aspect, a cutting guide for cutting bone in a surgical procedure is provided. Such a cutting guide comprises a body and a rotatable device. In some embodiments, the body comprises a top portion, a bottom portion parallel to the top portion, and a side portion connecting the top and the bottom portions. The rotatable device is coupled to one end of the top portion of the body, and comprises a pivotal element and a handle. The handle has a first portion coupled to the pivotal element, and a second portion configured to be rotated around an axis of the pivotal element. Each of the top portion of the body, the side portion of the body, the bottom portion of the body, and the handle has one respective edge providing a respective guide surface. The body of the cutting guide is configured to be positioned against a first bone and each respective guide surface is configured to receive a surgical tool for cutting the first bone.

In some embodiments, the axis of the pivotal element is perpendicular to a plane defined by the body of the cutting guide. The handle is movable at an angle, for example, in the range of from 0 to 60 degree, relative to an in-plane normal to the top portion of the body of the cutting guide. Each of the handle, the top portion of the body, the side portion of the body and the bottom portion of the body may have a surface being flat and coplanar to one another. In some embodiments, the body of the cutting guide and the handle defines a first slot, with an opening defined between the bottom portion of the body and the handle, when the handle is in a position away from the bottom portion of the body.

In some embodiments, the pivotal element comprises a device selected from a group consisting of a screw, a shoulder bolt, a dowel pin, a combination of a bolt and a nut, a wrenching device, a lock and gear device, and any combination thereof. The body of the cutting guide may define pin holes, for example, at least two pin holes. The pin holes are sized and configured to receive pins to couple the body to a bone. The handle may also define at least one pin hole, which is sized and configured to receive a pin to couple the handle to a bone.

The body and the rotatable device comprise a suitable material, for example, a metal material such as stainless steel.

In some embodiments, the body of the cutting guide further defines a second slot in the upper or bottom portion of the body. The second slot has at least one edge providing respective guide surface, and is configured to receive a surgical tool for cutting a second bone during a surgical procedure.

In another aspect, a kit comprising a cutting guide as described above and a surgical tool is provided. The surgical tool is configured for cutting a bone surface. In some embodiments, the surgical tool is selected from the group consisting of a high speed burr, a saw, an end cutting reamer and any combination thereof.

In another aspect, a method for using the cutting guide described above is also provided. In some embodiments, the method comprises the following steps: positioning the cutting guide against a first bone of a patient so that the respective edges provided by the body and the handle match with a predetermined region of the first bone of the patient; adjusting the rotatable device so that the handle is oriented to a patient-specific angle relative to the body of the cutting guide; and cutting the first bone in the predetermined region along the respective edges of the body and the handle after the rotatable device is adjusted. In some embodiments, the cutting guide is used in a surgery of total ankle arthroplasty. The first bone is tibia, and the handle of the rotatable device is aligned along and covering a medial malleolus.

In some embodiments, the method further comprises a step of fixing the cutting guide onto the first bone. The body of the cutting guide comprises at least two pin holes, and the cutting guide is coupled with the first bone by inserting at least two pins into the at least two pin holes. The method may also comprise a step of cutting a portion of a second bone, for example talus. The body of the cutting guide further defines a second slot in the bottom portion of the body and the second slot matches a portion of the second bone to be cut.

The cutting guide provided in the present disclosure, which comprises a rotatable device with an adjustable handle, provides a variable patient-specific angle according to a patient's bone structure. For example, in a surgical procedure of total ankle arthroplasty, the handle can be oriented along and covering medial or lateral malleolus to keep medial or lateral malleolus intact while tibia is cut.

BRIEF DESCRIPTION OF THE DRAWINGS

The present disclosure is best understood from the following detailed description when read in conjunction with the accompanying drawings. It is emphasized that, according to common practice, the various features of the drawings are not necessarily to scale. On the contrary, the dimensions of the various features are arbitrarily expanded or reduced for clarity. Like reference numerals denote like features throughout specification and drawings.

FIG. 12 is a plan view of another exemplary cutting guide with a rotatable device and pin holes in accordance with some embodiments.

FIG. 13 is a perspective view illustrating the cutting guide of FIG. 12.

FIG. 15 is a flow chart diagram illustrating an exemplary method of using a cutting guide as a part of a surgical procedure in accordance with some embodiments.

DETAILED DESCRIPTION

Figure 1:
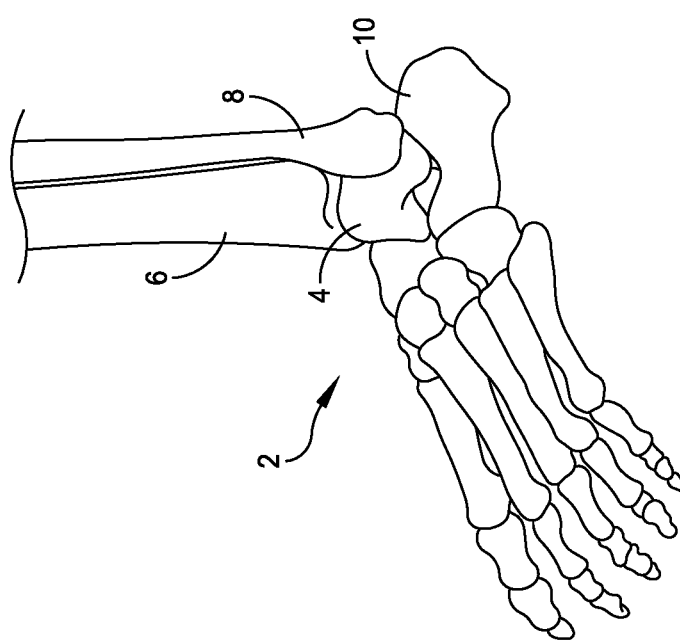
FIG. 1 illustrates an anatomic view of an ankle joint.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected," refer to a relationship wherein structures are secured or attached to one another either directly or indirectly through intervening structures, as well as both movable or rigid attachments or relationships, unless expressly described otherwise.

In the present disclosure the singular forms "a," "an," and "the" include the plural reference, and reference to a particular numerical value includes at least that particular value, unless the context clearly indicates otherwise. When values are expressed as approximations, by use of the antecedent "about," it will be understood that the particular value forms another embodiment. As used herein, "about X" (where X is a numerical value) preferably refers to ±10% of the recited value, inclusive. For example, the phrase "about 8" preferably refers to a value of 7.2 to 8.8, inclusive. Where present, all ranges are inclusive and combinable. For example, when a range of "1 to 5" is recited, the recited range should be construed as including ranges "1 to 4", "1 to 3", "1-2", "1-2 & 4-5", "1-3 & 5", "2-5", and the like. In addition, when a list of alternatives is positively provided, such listing can be interpreted to mean that any of the alternatives may be excluded, e.g., by a negative limitation in the claims. For example, when a range of "1 to 5" is recited, the recited range may be construed as including situations whereby any of 1, 2, 3, 4, or 5 are negatively excluded; thus, a recitation of "1 to 5" may be construed as "1 and 3-5, but not 2", or simply "wherein 2 is not included." It is intended that any component, element, attribute, or step that is positively recited herein may be explicitly excluded in the claims, whether such components, elements, attributes, or steps are listed as alternatives or whether they are recited in isolation.

In FIGS. 1-14, like items are indicated by like reference numerals, and for brevity, descriptions of the structure, provided above with reference to the preceding drawings, are not repeated.

The present disclosure provides a cutting or resection guide for cutting a bone during a surgical procedure. In accordance with some embodiments, a cutting guide is configured to provide an adjustable angle according to patient-specific bone structure. The cutting guide is used, for example, for cutting a bone such as tibia in a surgery of total ankle arthroplasty.

Figure 2:
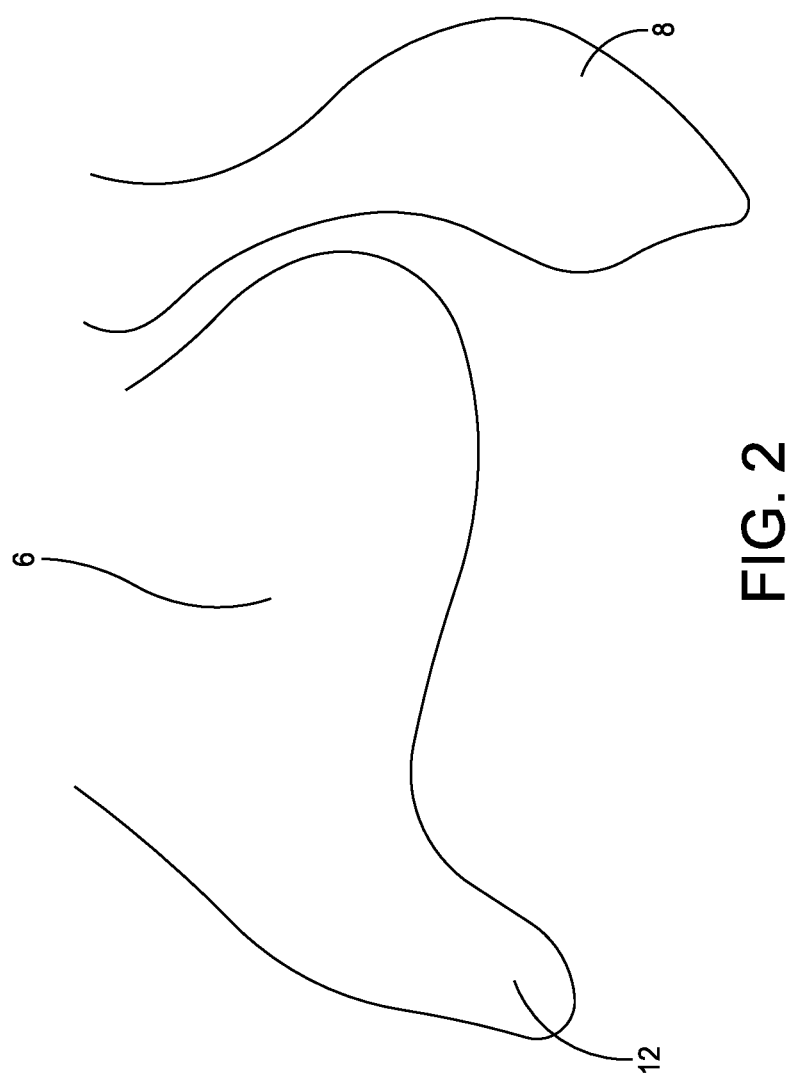
FIG. 2 is a plan view illustrating bones of an ankle joint.

Referring to FIG. 1, an ankle joint 2 comprises a talus 4 in contact with a tibia 6 and a fibula 8. A calcaneus 10 is located adjacent to the talus 4. In total ankle replacements, the talus 4 and the tibia 6 may be resected, or cut, to allow insertion of a talar implant and a tibial implant. Referring to FIG. 2, medial malleolus 12 is the medial surface of the lower extremity of tibia 6 prolonged downward. The talus (not shown) is below the tibia 6. Lower extremity of the fibula 8 is lateral malleolus. Different patients have different bone structures including, for example, medial malleolus 12 having different sizes and angles. It is desired that medial malleolus 12 is kept intact in total ankle replacement. Accidental cut or damage should be avoided.

Figure 3:
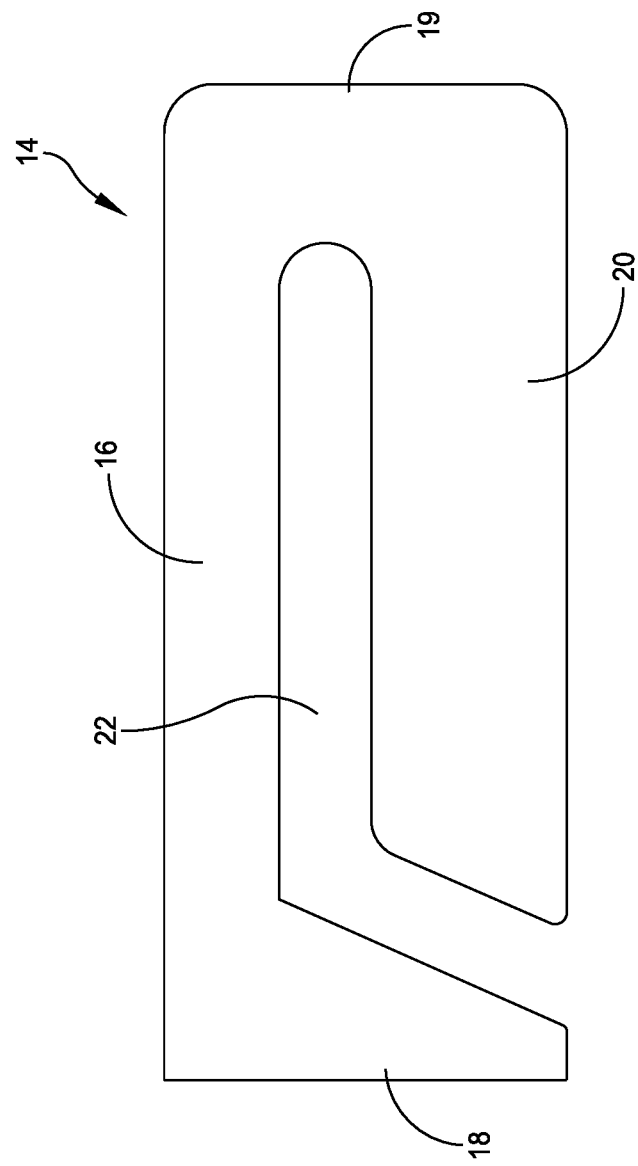
FIG. 3 is a plan view illustrating a cutting guide in one embodiment.

Referring to FIG. 3, a cutting guide 14 in one embodiment comprises a top portion 16, a bottom portion 20, a side portion 18 connected with the top portion 16, and a side portion 19 connecting the top portion 16 and the bottom portion 20. The cutting guide 14 defines a slot 22 with an opening. The cutting guide 14 can be placed against a bone, for example, a tibia 6 of a patient. The portion or region of the bone within slot 22 of the cutting guide 14 can be cut by moving a cutting tool along at least some portions of the edges of the slot 22. In the cutting guide 14, the top portion 16 and the side portion 18 may be oriented at a fixed angle, for example, 90 degree. However, different patients have various sized and angled medial malleolus 12. So when cutting guide 14 is used for cutting a tibia 6, it might be difficult to adjust and match the fixed angle of cutting guide 14 with the angle of medial malleolus 12 of a patient. Sometimes medial malleolus 12 could be partially damaged or even accidently cut if careful measure is not taken.

Figure 4:
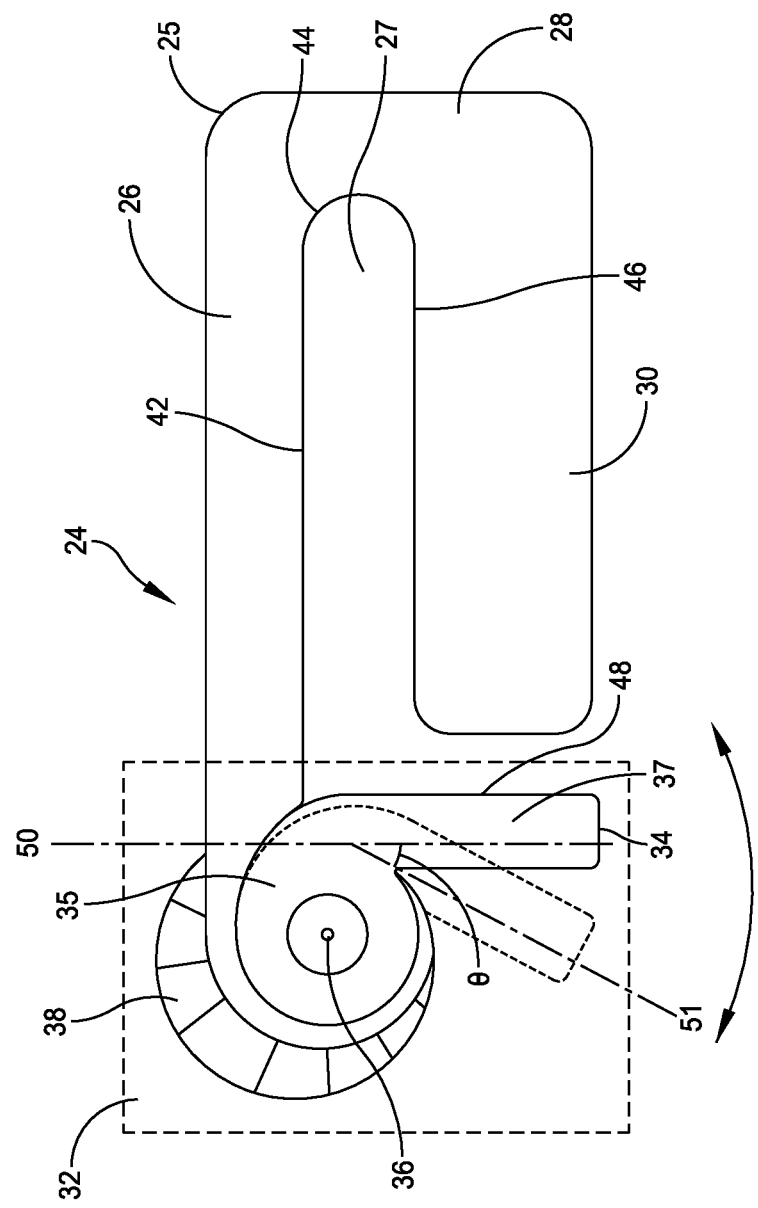
FIG. 4 is a plan view of an exemplary cutting guide with a rotatable device in accordance with some embodiments.

Referring to FIG. 4, an exemplary cutting guide 24 with a rotatable device 32 is provided in accordance with some embodiments. Such a cutting guide 24 comprises a body 25 and a rotatable device 32. The body 25 comprises a top portion 26, a side portion 28, and a bottom portion 30. The bottom portion 30 may be parallel to the top portion 26. The side portion 28 connects the top portion 26 and the bottom portion 30. The side portion 28 may be normal to the top and the bottom portions 26, 30 in some embodiments. The rotatable device 32 is coupled to one end of the top portion 26 of the body 25. Such an end of the top portion 26 may be opposite to the end connecting with side portion 28. The rotatable device 32 comprises a handle 34 and a pivotal element 36. The handle 34 has a first (or proximal) portion 35 coupled to the pivotal element 36, and a second (or distal) portion 37 configured to be rotated around an axis 40 of the pivotal element 36.

Figure 5:
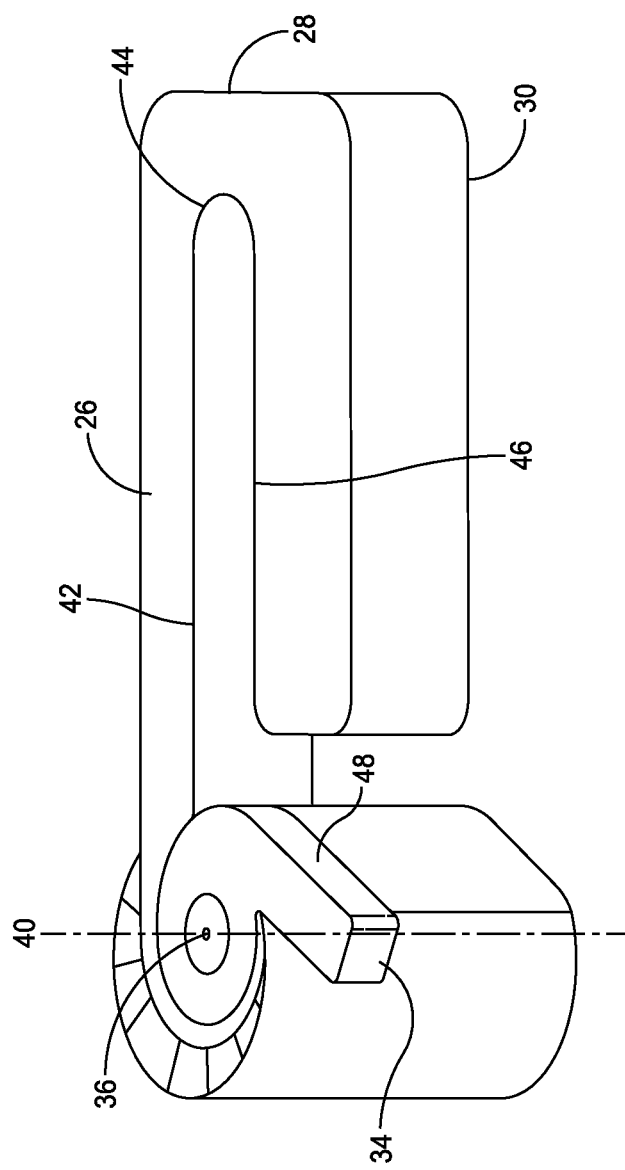
FIG. 5 is a perspective view of the cutting guide of FIG. 4.

Referring to FIG. 5, axis 40 is at the center of pivotal element 36 and normal to a top surface of the body 25 in some embodiments. The axis 40 of the pivotal element 36 is perpendicular to a plane defined by the body 25 of the cutting guide 24. Referring to FIG. 4, the handle 34 is movable at an angle ($\theta$) as shown in FIG. 4, relative to an in-plane normal 50 to the top portion 26 of the body 25 of the cutting guide 24. The handle 34 may have an axis 51 as illustrated in FIG. 4. For example, such an angle ($\theta$) may be in the range of from 0 to 60 degree (e.g., from 0 to 30 degree or from 0 to 45 degree). When the angle is zero, the second end 37 of the handle 34 is perpendicular to the top portion 26 of the body 25. The handle 34 is configured to move in a plane parallel to the top surface of the body in some embodiments.

Each of the top portion 26 of the body, the side portion 28 of the body and the bottom portion 30 of the body, and the handle 34 may have a surface being flat and coplanar to one another. Referring to FIG. 4, in some embodiments, the rotatable device 32 may optionally comprise a support 38. Each of the top portion 26 of the body, the side portion 28 of the body and the bottom portion 30 of the body, and the support 38 of the rotatable device 32 may have a coplanar flat surface, or have a concave surface configured to be easily placed against a bone.

Each of the top portion 26 of the body, the side portion 28 of the body, the bottom portion 30 of the body, and the handle 34 has one respective edge providing a respective guide surface. The respective edges for respective guide surface are labelled as edges 42, 44, 46 and 48 as shown in FIG. 4 and FIG. 5. The body 25 of the cutting guide 24 is configured to be positioned against a first bone and each respective guide surface is configured to receive a surgical tool for cutting the first bone (for example, tibia 6). In some embodiments, the body 25 of the cutting guide 24 and the handle 34 defines a first slot 27, with an opening defined between the bottom portion 30 of the body and the handle 34 as illustrated in FIG. 4, when the handle 34 is in a position away from the bottom portion 30 of the body 25.

The pivotal element 36 comprises a device coupled with the handle 34. Examples of a suitable device in the pivotal element 36 include but are not limited to a screw, a shoulder bolt, a dowel pin, a combination of a bolt and a nut, a wrenching device, a lock and gear device, and any combination thereof. The device for pivotal element 36 may be continuously moved to adjust the angle ($\theta$) and can self-lock when the desired angle is obtained. In some other embodiments, the device may be unscrewed for a suitable angle ($\theta$) and then tightened. In some embodiments, cutting guide 24 as illustrated in FIG. 4 and FIG. 5 may be sized and configured to be fit with and be fixed to an external jig or any other suitable means during a surgery. In some other embodiments, cutting guide 24 as illustrated in FIG. 4 and FIG. 5 may comprise pinholes 52 as illustrated in FIG. 6.

Figure 6:
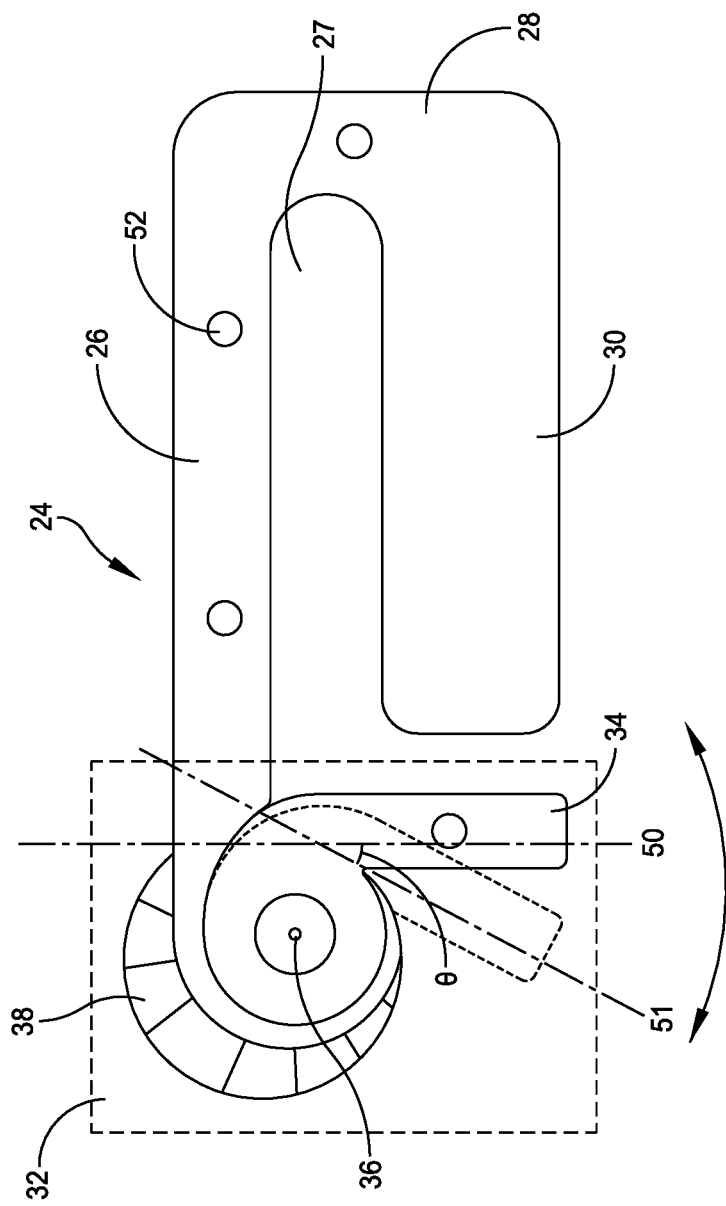
FIG. 6 is a plan view of an exemplary cutting guide with a rotatable device and pin holes in accordance with some embodiments.
Figure 7:
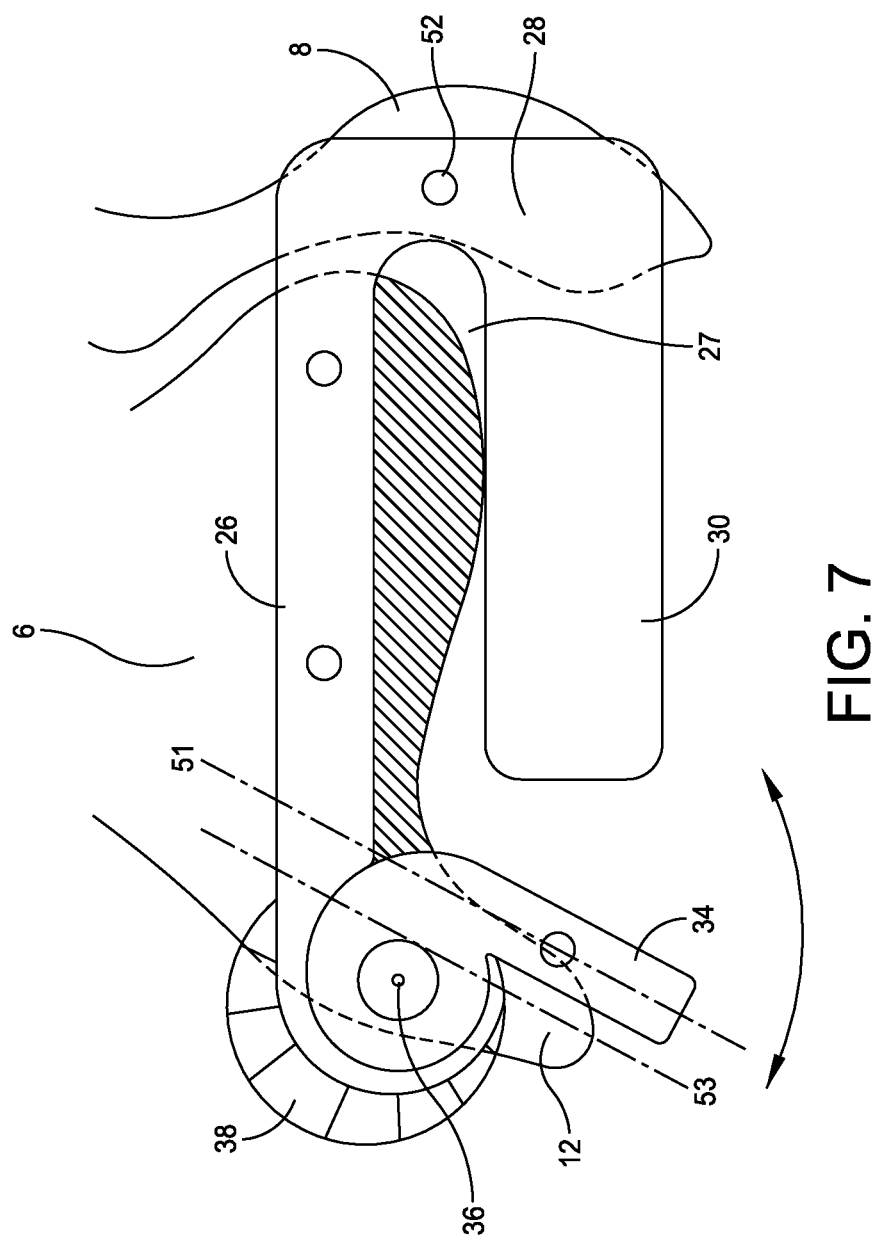
FIGS. 7-8 are plan views illustrating the cutting guide of FIG. 6 positioned against a tibia and a fibula of a patient for cutting the tibia in some embodiments.

Referring to FIG. 6, cutting guide 24 include pinholes 52 in accordance with some embodiments. For example, the body 25 of cutting guide 24 may define pin holes 52, for example, at least two pin holes 52. The pin holes 52 are sized and configured to receive pins to couple the body 25 to a bone (by inserting pins into the pinholes 52 and the bone), when the cutting guide 24 is placed on or against a bone (as shown in FIG. 7). The handle 24 may also define at least one pin hole 52, which is sized and configured to receive a pin to couple the handle 34 to a bone during a surgical procedure.

The body 25 and the rotatable device 32 comprise a suitable material, for example, a metal material such as stainless steel, or an engineering plastic material or combinations thereof. The body 25 and the rotatable device 32 are made of stainless steel in some embodiments. The body 25 and the rotatable device 32 may comprise a radiopaque material.

Figure 9:
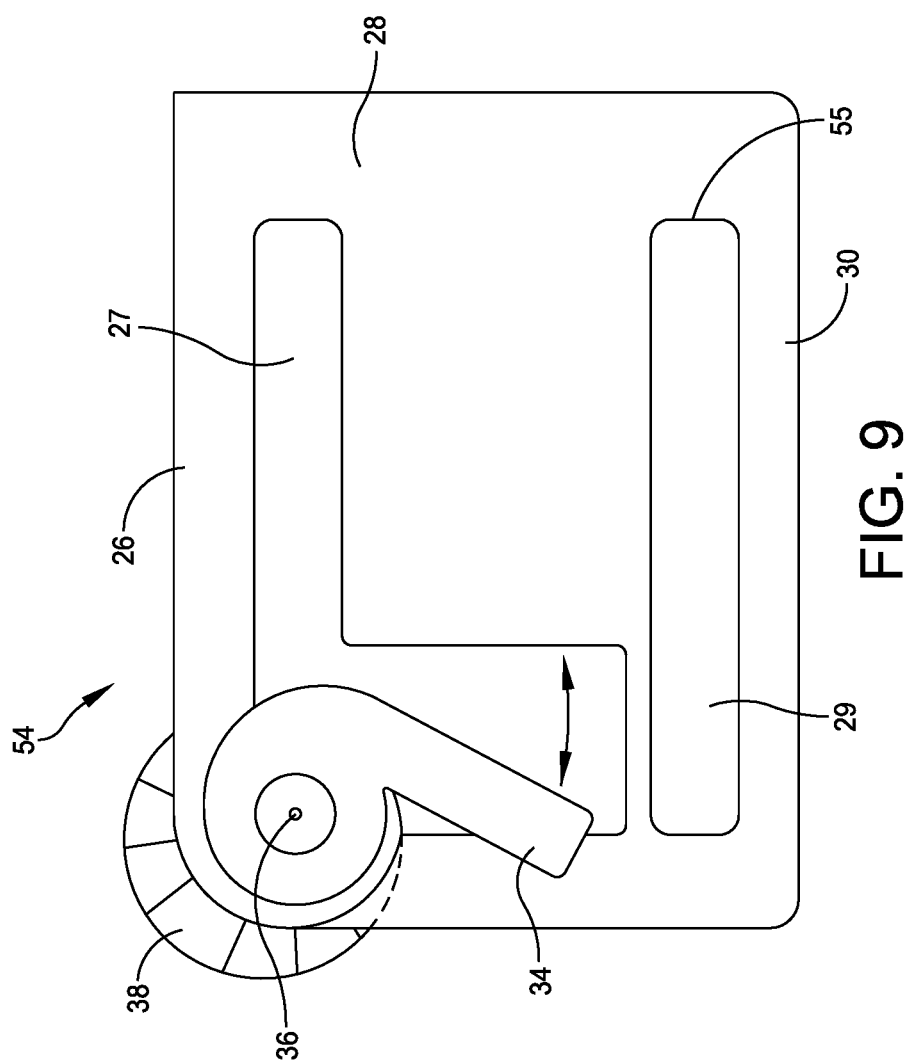
FIG. 9 is a plan view illustrating an exemplary cutting guide with a rotatable device and a body defining a first slot and a second slot, for cutting a tibia and a talus, respectively, in accordance with some embodiments.
Figure 10:
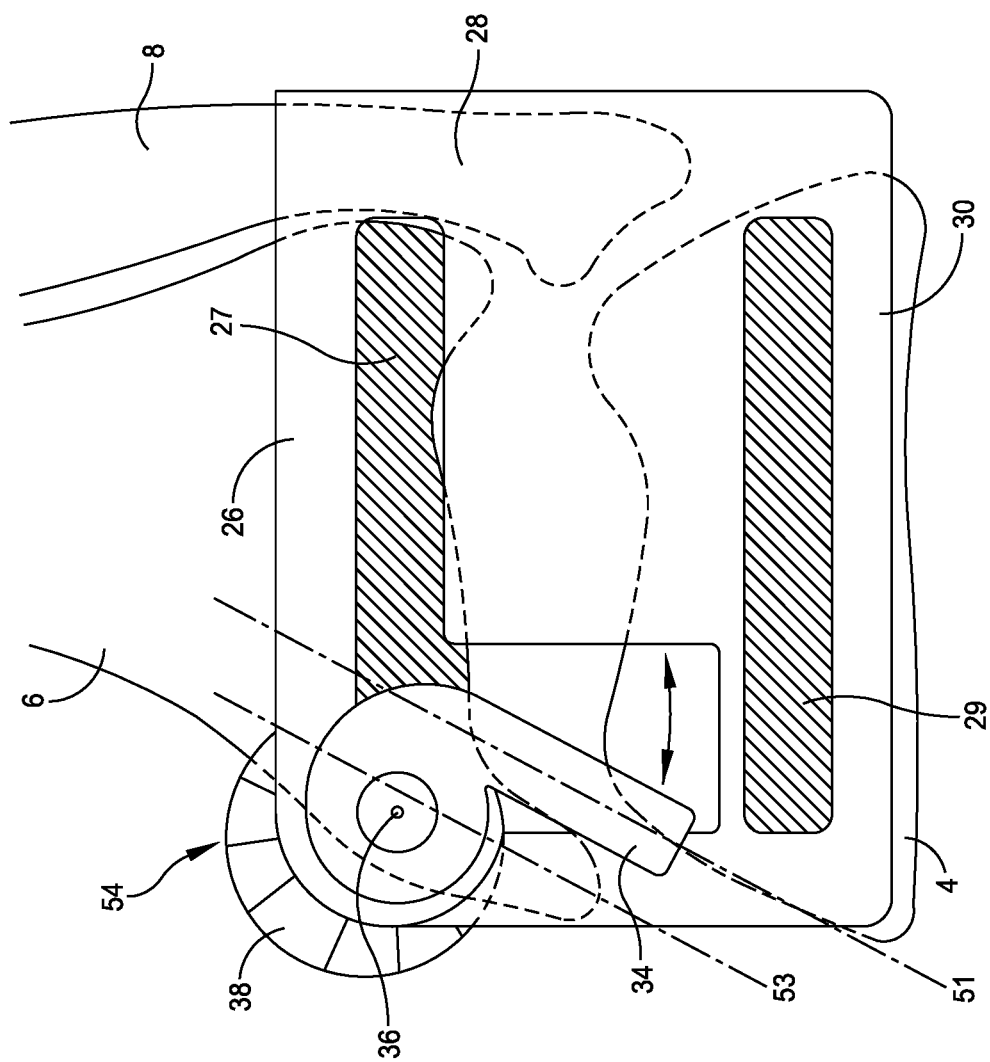
FIG. 10 illustrates the cutting guide of FIG. 9 positioned against a tibia, a talus and a fibula of a patient's left foot for cutting the tibia and the talus in some embodiments.

Referring to FIG. 9, an exemplary cutting guide 54 comprises a rotatable device 32 and a body 25 defining a first slot 27 and a second slot 29, for cutting a first bone (e.g., a tibia 6) and a second bone (e.g., a talus 4), respectively, in accordance with some embodiments. Cutting guide 54 has the structural features as described above. The body 25 of the cutting guide 54 further defines the second slot 29 in the upper or bottom portion of the body 25. The second slot 29 has at least one edge 55 providing respective guide surface. Referring to FIGS. 9 and 10 as discussed herein, the second slot 29 is configured to receive a surgical tool for cutting the second bone (e.g., a talus 4) during a surgical procedure.

Referring to FIGS. 12 and 13, another exemplary cutting guide 60 in accordance with some embodiments is illustrated. Cutting guide 60 has the structural features of cutting guide 24 as described above. In addition, the top portion 26 of the body 25 of the cutting guide 60 defines additional features as shown used as an alignment tool, which help orient the cut guide 60 to an intramedullary guided rod (not shown). A general alignment method for preparing a total ankle replacement is described in INBONE® II Total Ankle System Surgical Technique, which is available from Wright Medical Group (Memphis, Tenn.), and is incorporated by reference herein in its entirety. Two holes 62 on either side are configured to fix the cutting guide 60 onto an external fixture, which are attached with two screws. Similar to holes 52 on cutting guide 24, at least two holes 64 are configured to accept K-wires or pins for fixing the cutting guide 60 to a bone. The slots 66 and 68 are configured to lighten the cutting guide and provide visibility during fluoroscopy so that the underlying bone and the cutting guide 60 and their position can be seen.

Figure 14:
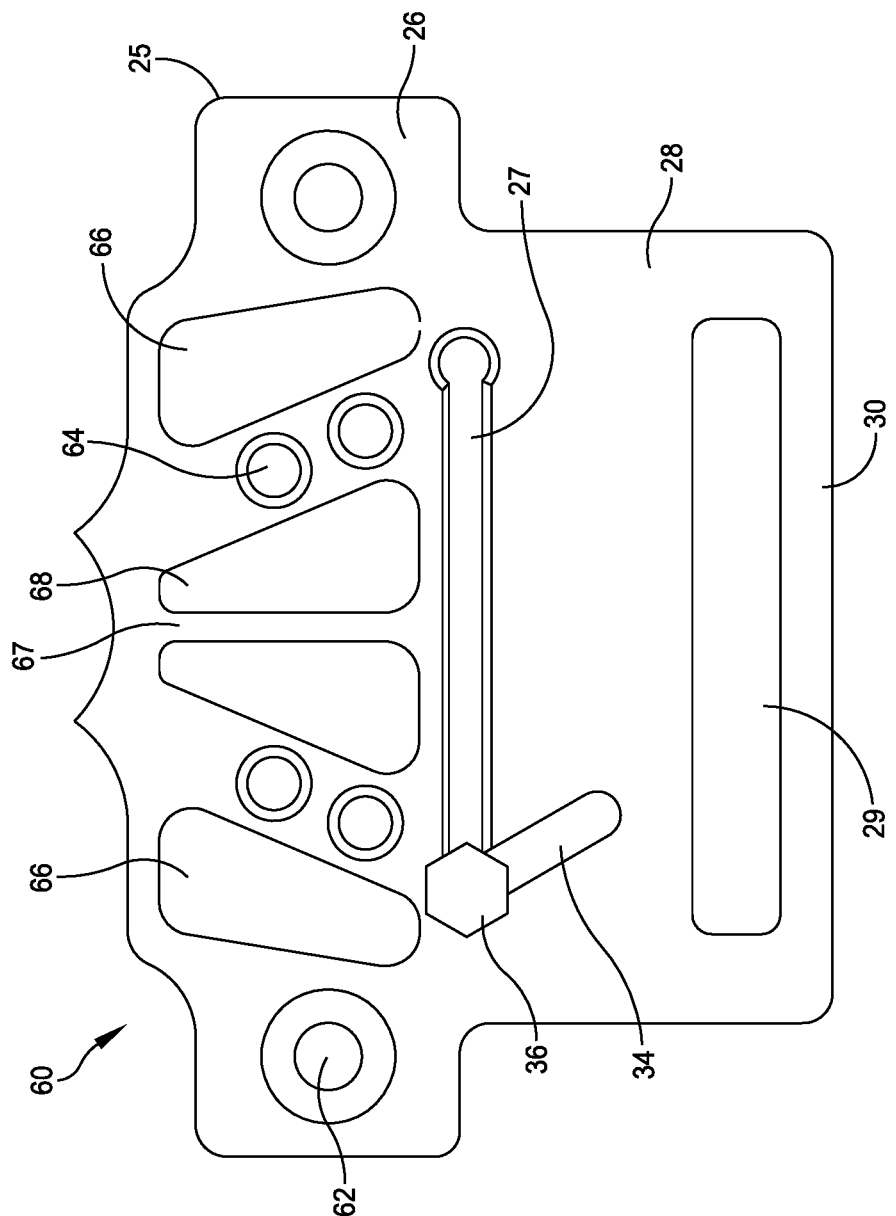
FIG. 14 is a plan view illustrating another exemplary cutting guide with a rotatable device, pin holes and a body defining a first slot and a second slot, for cutting a tibia and a talus, respectively, in accordance with some embodiments.

Referring to FIG. 14, another exemplary cutting guide 60 is illustrated. Cutting guide 60 of FIG. 14 has the structural features of cutting guide of FIGS. 12-13 as described above. Cutting guide 60 of FIG. 14 comprises a rotatable device 32 comprising a handle 34 and a pivotal element 36, holes 62, 64, and a body 25 defining a first slot 27. In addition, the body 25 further defines a second slot 29. The two slots 27 and 29 are for cutting two bones, for example, a tibia and a talus, respectively, in accordance with some embodiments.

In another aspect, the present disclosure provides a kit comprising a cutting guide as described above (24, 54, or 60) and a surgical tool for cutting a bone is provided. The surgical tool is configured for cutting a bone (by cutting through the surface). Such a cutting guide (24, 54, or 60) comprises a body 25 and a rotatable device 32. The body 25 comprises a top portion 26, a side portion 28, and a bottom portion 30 parallel to the top portion. The side portion 28 connects the top and the bottom portions 26, 28. The rotatable device 32 is coupled to one end of the top portion of the body, and comprises a pivotal element 36 and a handle 34. The handle 34 has a first portion 35 coupled to the pivotal element 36 and a second portion 37 configured to be rotated around an axis 40 of the pivotal element 32. Each of the top portion 26 of the body 25, the side portion 28 of the body 25, the bottom portion 30 of the body 25, and the handle 34 has one respective edge providing a respective guide surface. The body 25 of the cutting guide (24, 54, or 60) may also define a second slot 29 in the bottom or upper portion of the body. The pivotal element 36 comprises a device selected from a group consisting of a screw, a shoulder bolt, a dowel pin, a combination of a bolt and a nut, a wrenching device, a lock and gear device, and any combination thereof. In some embodiments, the body 25 defines at least two pin holes 52 sized and configured to receive pins to couple the body 25 of the cutting guide to the bone. The body 25 and the rotatable device 32 each comprise a suitable material such as a metal (e.g., stainless steel). In some embodiments, the surgical tool is selected from the group consisting of a high speed burr, a saw, an end cutting reamer and any combination thereof.

Referring to FIG. 15, an exemplary method 70 of using a cutting guide as a part of a surgical procedure in accordance with some embodiments is illustrated.

At step 72, the cutting guide (e.g., 24, 54, or 60) as described above is positioned (or placed) against a first bone (e.g., tibia) of a patient so that the respective edges provided by the body 25 and the handle 34 match with a predetermined region of the first bone of the patient. The cutting guide can be also placed against a second bone having a portion to be cut, or other bones not to be cut. Preoperative assessment of the appropriate size and position of the tibial and talar components will provide intraoperative guidance. Preoperative templating and radiographic overlays can be used to estimate and identify the bone structure of a patient and the predetermined region or regions to be cut. Final implant size and position can be determined intraoperatively through direct visualization under fluoroscopic assistance. General methods for operation preparation and alignment in a total ankle replacement are described in INBONE® II Total Ankle System Surgical Technique, which is incorporated by reference herein in its entirety.

Figure 8:
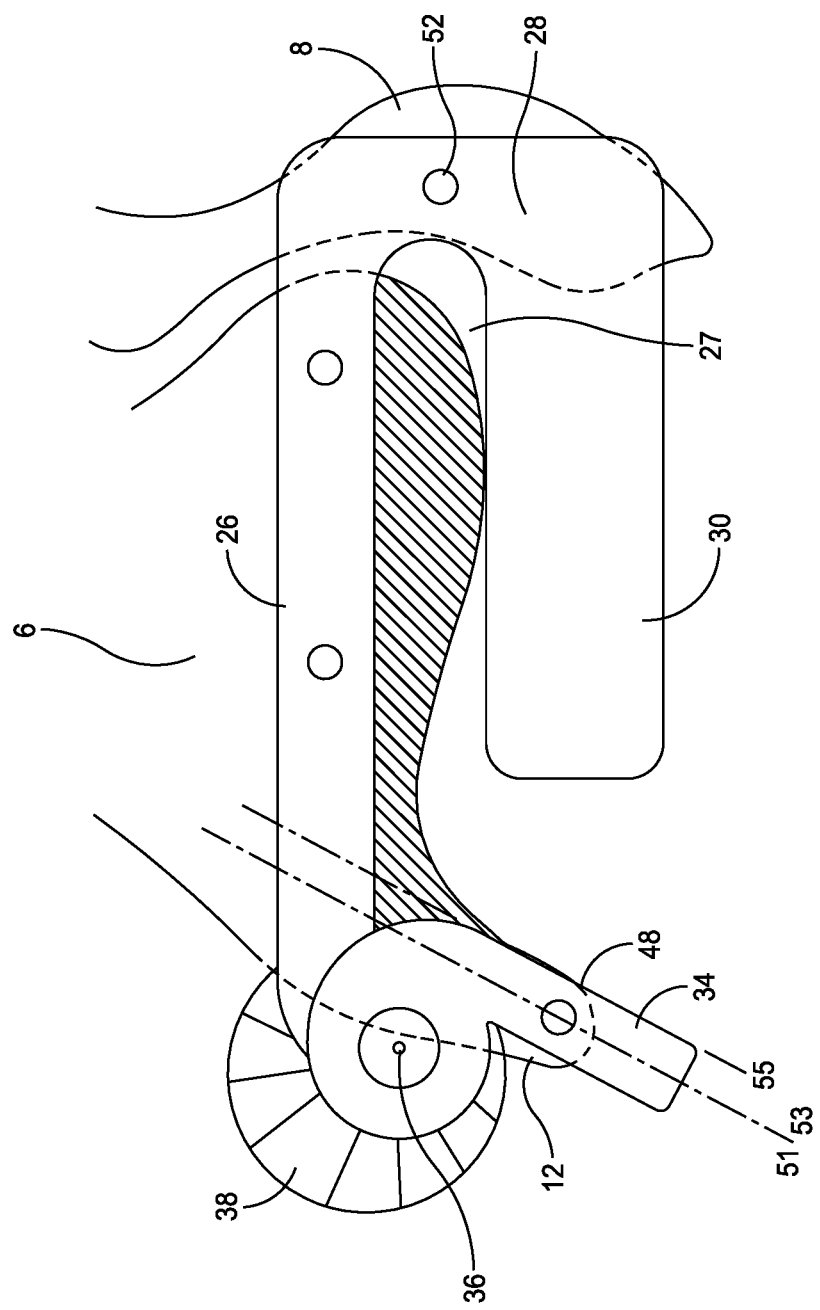

The cutting guide (e.g., 24, 54, or 60) are aligned properly to bones of a patient including talus 4 and tibia 6, by defining six degrees of freedom including three rotations and three translations. The degrees of freedom for rotations include flexion/extension, internal/external, and varus/valgus. The degrees of freedom for translations include anterior/posterior, medial/lateral, and proximal/distal. The internal/external rotation can be determined from medial/lateral malleoli of the ankle joint 2. A surgeon may bisect the medial/lateral malleoli to provide an angle, or use an angle of the medial malleolus. An angle for the flexion/extension rotation may be determined by referencing to tibia 6. The cutting guide (e.g., 24, 54, or 60) needs to be positioned so that the cut having a top cutting line or surface (as shown in FIGS. 7 and 8) is perpendicular to the center of the tibial axis in some embodiments. The varus/valgus rotation can be determined by placing the foot in the plantigrade position and making parallel cut aligned with a mechanical axis of tibia 6.

The translations for the cutting guide (e.g., 24, 54, or 60) may be determined through creating a cut to a damaged bone or bones while preserving the maximum amount of good bones. The medial/lateral position of the cut guide (e.g., 24, 54, or 60) may be determined by having a maximum tibial cut as allowable without interfering the medial malleolus and fibula. The proximal/distal placement of the cut guide (e.g., 24, 54, or 60) is determined by removing a minimum amount of bone for putting a minimal implant construct height. The anterior/positioner placement of the cutting guide may be necessary to ensure that the center of rotation of the talus 4 is positioned underneath the tibia 6.

At step 72, the rotatable device 32 with handle 34 is adjusted so that handle 34 is oriented to a patient-specific angle relative to the body 25 of the cutting guide. In embodiments, an edge 48 of handle 34 is aligned with and parallel to the longitudinal axis 53 of the medial malleolus 12. The edge 48 of handle 34 may be positioned laterally, medially or along the same longitudinal axis as the medial malleolus longitudinal axis 53. Referring to FIG. 4, for example, the handle 34 is rotated at an angle (θ) relative to an in-plane normal 50 to the top portion 26 of the body 25 of the cutting guide 24. Such an angle (θ) may be in the range of from 0 to 60 degree (e.g., from 0 to 30 degree or from 0 to 45 degree). Handle 34 is then fixed or automatically locks after step 72. In some embodiments, the pivotal element 36 may need to be tightened depending on the mechanism of the rotatable device 32, for example, if pivotal element 36 comprises a screw which may be loosened during step 72.

In some embodiments, the cutting guide (e.g., 24, 54, or 60) is used in a surgery of total ankle arthroplasty. The first bone is tibia 6. Tibial plateau as shown for example, in FIG. 7 and FIG. 8, is to be cut. The medial malleolus is to be protected, without any cutting or damage. Referring to FIG. 7, the cutting guide 24 is placed over or against a tibia 6 and a fibula 8 of a patient for cutting the tibia in some embodiments. The handle 34 of the rotatable device 32 is aligned along and covering a medial malleolus 12. The side portion 28 of the body 25 of the cutting guide 24 is placed close to and/or covers the fibula 8, which is not to be cut. The shaded areas in FIG. 7 (and FIGS. 8, 10-11) illustrate the portions of the bone(s) to be cut. Referring to FIG. 8, the edge 48 of the handle 34 (illustrated with extension dot line 55) is parallel to the longitudinal axis 53 of the medial malleolus 12. In some embodiments, the axis 51 of the handle 34 may be overlapped with or is proximal to the longitudinal axis 53 of the medial malleolus 12.

Figure 11:
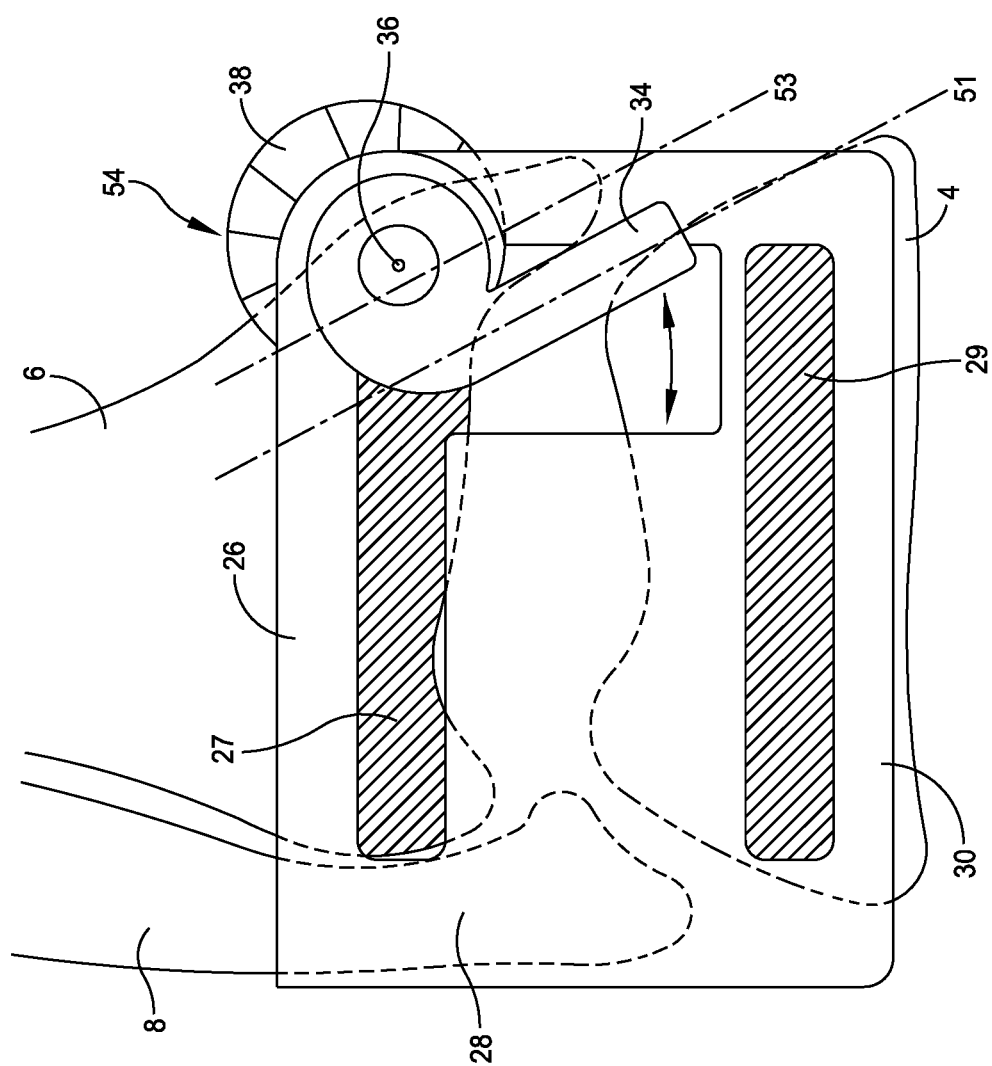
FIG. 11 is a plan view illustrating the cutting guide of FIG. 9 positioned against a tibia, a talus and a fibula of a patient's right foot for cutting the tibia and the talus in some embodiments.

Referring to FIG. 10 and FIG. 11, the cutting guide 54 is placed over or against a talus 4, a tibia 6 and a fibula 8 of a patient for cutting the tibia 6 and the talus 4 in some embodiments. In FIG. 10 the cutting guide 54 is positioned against a tibia, a talus and a fibula of a patient's left foot. In FIG. 11, the cutting guide 54 is positioned against a tibia, a talus and a fibula of a patient's right foot.

The handle 34 of the rotatable device 32 is aligned with a longitudinal axis 53 of the medial malleolus 12. The side portion 28 of the body 25 of the cutting guide 24 is placed close to and/or covers the fibula 8, which is not to be cut. The tibia 6 falling within the first slot 27 (as shown in a shaded region) is to be cut for a space for a tibial implant. The talus 4 falling within the second slot 29 (shaded region) is to be cut for a space for a talar implant. Cutting tools are within the purview of those skilled in the art and include, but are not limited to, sawblades, reamers, drills, osteotomes, burrs and the like. It should be noted that the tibial implant and the talar implant are two component of a total ankle replacement.

At step 76, which is optional, the cutting guide (e.g., 24, 54, or 60) is fixed onto the first bone. The body 25 of the cutting guide (e.g., 24, 54, or 60) comprises at least two pin holes (52 or 62 or 64). The cutting guide is coupled with the first bone by inserting at least two pins into the at least two pin holes.

At step 78, a portion of the first bone (e.g., tibia) is cut in the predetermined region along the respective edges of the body 25 and the handle 34 after the rotatable device 32 is adjusted. Referring to FIGS. 7-8 and 10-11, the portion of the tibia 6 falling within the first slot 27 is cut for a space for installing a tibial implant. The cutting can be performed using a suitable surgical tool. Examples of a suitable surgical tool include but are not limited to a high speed burr, a saw, an end cutting reamer and any combination thereof At step 80, a portion of a second bone, for example talus 4, is cut in some embodiments. This step is optional depending on the type of cutting guide. For example, the body of the cutting guide 54 further defines a second slot 29 in the bottom portion 30 of the body 25 and the second slot 29 matches a portion of the second bone to be cut. Referring to FIGS. 10 and 11, a portion of the talus 4 falling within the second slot 29 is cut for a space for installing a talar implant. The cutting can be performed using a suitable surgical tool Examples of a suitable surgical tool include but are not limited to a high speed burr, a saw, an end cutting reamer and any combination thereof.

The present disclosure also provides a method of making the cutting guide. The cutting guide can be made using any suitable method. For example, the body and the parts for the rotatable device can be separately molded from a suitable material such as stainless steel, and then machined and assembled to form a resulting cutting guide.

The cutting guide provided in the present disclosure comprises a rotatable device with an adjustable handle, and provides a variable patient-specific angle according to a patient's bone structure. In a surgical procedure of total ankle arthroplasty, the handle can be oriented along and covering medial or lateral malleolus to keep medial or lateral malleolus intact while either tibia or talus is cut.

Although the subject matter has been described in terms of exemplary embodiments, it is not limited thereto. Rather, the appended claims should be construed broadly, to include other variants and embodiments, which may be made by those skilled in the art.

What is claimed is:

1. A cutting guide, comprising:
 a body comprising a top portion, a bottom portion, and a side portion connecting the top and the bottom portions; and
 a rotatable device coupled to one end of the top portion of the body, the rotatable device comprising a pivotal element and a handle, the handle having a first portion coupled to the pivotal element and a second portion configured to be rotated around an axis of the pivotal element,
 wherein each of the top portion of the body, the side portion of the body, the bottom portion of the body, and the handle has one respective edge providing a respective guide surface.

2. The cutting guide of claim 1, wherein the body of the cutting guide is configured to be positioned against a first bone and the respective guide surfaces of the top portion, the side portion and the bottom portion of the body are so configured that a surgical tool is received for cutting the first bone.

3. The cutting guide of claim 1, wherein the axis of the pivotal element is perpendicular to a plane defined by the body of the cutting guide, and the handle is movable at an angle in a range of from 0 to 60 degree relative to an in-plane normal to the top portion of the body of the cutting guide.

4. The cutting guide of claim 1, wherein each of the handle, the top portion of the body, the side portion of the body and the bottom portion of the body has a surface being flat and coplanar to one another.

5. The cutting guide of claim 1, wherein the body of the cutting guide and the handle defines a first slot, with an opening defined between the bottom portion of the body and the handle when the handle is in a position away from the bottom portion of the body.

6. The cutting guide of claim 1, wherein the pivotal element comprises a device selected from a group consisting of a screw, a shoulder bolt, a dowel pin, a combination of a bolt and a nut, a wrenching device, a lock and gear device, and any combination thereof.

7. The cutting guide of claim 1, wherein the body defines at least two pin holes sized and configured to receive pins to couple the body to a bone.

8. The cutting guide of claim 1, wherein the handle defines at least one pin hole sized and configured to receive a pin to couple the handle to a bone.

9. The cutting guide of claim 1, wherein the bottom portion of the body is parallel to the top portion of the body.

10. The cutting guide of claim 1, wherein the body of the cutting guide further defines a second slot in the bottom portion of the body.

11. A method of using the cutting guide of claim 1, comprising:
 positioning the cutting guide against a first bone of a patient so that the respective edges provided by the body and the handle match with a predetermined region of the first bone of the patient;
 adjusting the rotatable device so that the handle is oriented to a patient-specific angle relative to the body of the cutting guide; and
 cutting the first bone in the predetermined region along the respective edges of the body and the handle after the rotatable device is adjusted.

12. The method of claim 11, wherein the cutting guide is used in a surgery of total ankle arthroplasty, the first bone is a tibia, and the handle of the rotatable device is aligned along and covering a medial malleolus.

13. The method of claim 11, further comprising:
 fixing the cutting guide onto the first bone, wherein the body of the cutting guide comprises at least two pin holes, and the cutting guide is coupled with the first bone by inserting at least two pins into the at least two pin holes.

14. The method of claim 11, further comprising:
cutting a portion of a second bone, wherein the body of the cutting guide further defines a second slot in the bottom portion of the body and the second slot matches a portion of the second bone to be cut.

15. The method of claim 14, wherein the second bone is a talus.

16. A kit, comprising:
a cutting guide comprising:
   a body comprising a top portion, a bottom portion, and a side portion connecting the top and the bottom portions, and
   a rotatable device coupled to one end of the top portion of the body, the rotatable device comprising a pivotal element and a handle, the handle having a first portion coupled to the pivotal element and a second portion configured to be rotated around an axis of the pivotal element, wherein each of the top portion of the body, the side portion of the body, the bottom portion of the body, and the handle has one respective edge providing a respective guide surface; and;
a surgical tool configured for cutting a bone surface.

17. The kit of claim 16, wherein the pivotal element comprises a device selected from a group consisting of a screw, a shoulder bolt, a dowel pin, a combination of a bolt and a nut, a wrenching device, a lock and gear device, and any combination thereof.

18. The kit of claim 16, wherein the body defines at least two pin holes sized and configured to receive pins to couple the body to the bone.

19. The kit of claim 16, wherein the bottom portion of the body is parallel to the top portion of the body.

20. The kit of claim 16, wherein the surgical tool is selected from the group consisting of a high speed burr, a drill, an osteotome, a sawblade, a cutting reamer and any combination thereof.

* * * * *